(12) United States Patent
Yencho et al.

(10) Patent No.: US 6,966,920 B2
(45) Date of Patent: Nov. 22, 2005

(54) SUTURELESS CLOSURE FOR CONNECTING A BYPASS GRAFT TO A TARGET VESSEL

(75) Inventors: Stephen A. Yencho, Menlo Park, CA (US); Michael Hendricksen, Menlo Park, CA (US); Jaime Vargas, Palo Alto, CA (US); Jamey Nielsen, San Francisco, CA (US); Bernard A. Hausen, Menlo Park, CA (US); Scott Vance, Cary, NC (US)

(73) Assignee: Cardica, Inc., Redwood City, CA (US)

( * ) Notice: Subject to any disclaimer, the term of this patent is extended or adjusted under 35 U.S.C. 154(b) by 471 days.

(21) Appl. No.: 10/331,356

(22) Filed: Dec. 30, 2002

(65) Prior Publication Data

US 2003/0120293 A1 Jun. 26, 2003

Related U.S. Application Data

(63) Continuation of application No. 09/705,819, filed on Nov. 6, 2000, now Pat. No. 6,537,287, which is a continuation of application No. 09/330,244, filed on Jun. 4, 1999, now Pat. No. 6,179,849.

(51) Int. Cl.[7] .............................................. A61B 17/04
(52) U.S. Cl. ...................................... 606/153; 606/155
(58) Field of Search .......................................... 606/153

(56) References Cited

U.S. PATENT DOCUMENTS

| | | |
|---|---|---|
| 3,254,650 A | 6/1966 | Collito |
| 3,519,187 A | 7/1970 | Kapitanov et al. |
| 3,774,615 A | 11/1973 | Lim et al. |
| 4,233,981 A * | 11/1980 | Schomacher ................ 606/153 |
| 4,294,255 A * | 10/1981 | Geroc ........................ 606/153 |
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |
| 4,503,568 A | 3/1985 | Madras |
| 4,523,592 A * | 6/1985 | Daniel ........................ 606/153 |
| 4,553,542 A | 11/1985 | Schenck et al. |
| 4,593,693 A | 6/1986 | Schenck |
| 4,607,637 A | 8/1986 | Berggren et al. |
| 4,624,255 A | 11/1986 | Schenck et al. |
| 4,624,257 A | 11/1986 | Berggren et al. |
| 4,657,019 A | 4/1987 | Walsh et al. |
| 4,665,906 A | 5/1987 | Jervis |
| 4,747,407 A | 5/1988 | Liu et al. |
| 4,907,591 A | 3/1990 | Vasconcellos et al. |

(Continued)

FOREIGN PATENT DOCUMENTS

| | | |
|---|---|---|
| WO | 97/31575 | 9/1997 |
| WO | 99/39643 | 8/1999 |

*Primary Examiner*—Gary Jackson
(74) *Attorney, Agent, or Firm*—Brian A. Schar

(57) ABSTRACT

The anastomosis device according to the present invention is a one piece device for connecting a graft vessel to a target vessel without the use of conventional sutures. The anastomosis device includes a frame for receiving and holding the end of a graft vessel in an everted position and first and second spreading members configured to be inserted into an opening in the target vessel. The first and second spreading members are arranged substantially in a plane for insertion into an opening in a target vessel, and are moved away from one another to capture the edges of the opening in the target vessel securing the graft vessel to the target vessel. One version of the anastomosis device includes a plurality of linkages arranged in two rows for grasping opposite sides of an opening in the target vessel. A portion of the linkages fold outward to trap vessel walls on opposite sides of the opening in the target vessel. The anastomosis devices greatly increases the speed with which anastomosis can be performed over known suturing methods.

7 Claims, 12 Drawing Sheets

U.S. PATENT DOCUMENTS

| | | |
|---|---|---|
| 4,917,087 A | 4/1990 | Walsh et al. |
| 4,917,090 A | 4/1990 | Berggren et al. |
| 4,917,091 A | 4/1990 | Berggren et al. |
| 5,062,842 A | 11/1991 | Tiffany |
| 5,119,983 A | 6/1992 | Green et al. |
| 5,217,474 A | 6/1993 | Zacca et al. |
| 5,234,447 A | 8/1993 | Kaster et al. |
| 5,250,058 A * | 10/1993 | Miller et al. ................. 606/154 |
| 5,250,060 A | 10/1993 | Carbo et al. |
| 5,304,220 A | 4/1994 | Maginot |
| 5,314,468 A | 5/1994 | Ramos Martinez |
| 5,336,233 A * | 8/1994 | Chen .......................... 606/153 |
| 5,366,462 A | 11/1994 | Kaster et al. |
| 5,395,311 A | 3/1995 | Andrews |
| 5,443,497 A | 8/1995 | Venbrux |
| 5,456,712 A | 10/1995 | Maginot |
| 5,456,714 A | 10/1995 | Owen |
| 5,464,449 A | 11/1995 | Ryan et al. |
| 5,478,354 A | 12/1995 | Tovey et al. |
| 5,522,834 A | 6/1996 | Fonger et al. |
| 5,556,405 A | 9/1996 | Lary |
| 5,558,667 A | 9/1996 | Yarborough et al. |
| 5,562,241 A | 10/1996 | Knodel et al. |
| 5,571,167 A | 11/1996 | Maginot |
| 5,643,340 A | 7/1997 | Nunokawa |
| 5,669,918 A | 9/1997 | Balazs et al. |
| 5,676,670 A | 10/1997 | Kim |
| 5,693,088 A | 12/1997 | Lazarus |
| 5,695,504 A | 12/1997 | Gifford, III et al. |
| 5,702,412 A | 12/1997 | Popov et al. |
| 5,707,380 A | 1/1998 | Hinchliffe et al. |
| 5,725,544 A | 3/1998 | Rygaard |
| 5,725,553 A | 3/1998 | Moenning |
| 5,797,920 A | 8/1998 | Kim |
| 5,817,113 A | 10/1998 | Gifford, III et al. |
| 5,868,763 A | 2/1999 | Spence et al. |
| 5,904,697 A | 5/1999 | Gifford, III et al. |
| 6,036,703 A * | 3/2000 | Evans et al. ................. 606/153 |
| 6,187,019 B1 | 2/2001 | Stefanchik |
| 6,514,263 B1 | 2/2003 | Stefanchik |
| 6,520,973 B1 | 2/2003 | McGarry |
| 6,530,932 B1 | 3/2003 | Swayze |

* cited by examiner

SUTURELESS CLOSURE FOR CONNECTING A BYPASS GRAFT TO A TARGET VESSEL

This application is a continuation of application Ser. No. 09/705,819 filed No. Nov. 6, 2000, now U.S. Pat. No. 6,537,287, which in turn is a continuation of application Ser. No. 09/330,244 filed Jun. 4, 1999, now U.S. Pat. No. 6,179,849, which is hereby incorporated by reference herein in its entirety.

BACKGROUND OF THE INVENTION

1. Field of the Invention

The invention relates to an anastomosis device and method, and more particularly, the invention relates to an anastomosis device for forming a sutureless connection between a bypass graft and a blood vessel.

2. Brief Description of the Related Art

Vascular anastomosis is a procedure by which two blood vessels within a patient are surgically joined together. Vascular anastomosis is performed during treatment of a variety of conditions including coronary artery disease, diseases of the great and peripheral vessels, organ transplantation, and trauma. In coronary artery disease (CAD) an occlusion or stenosis in a coronary artery interferes with blood flow to the heart muscle. Treatment of CAD involves the grafting of a vessel in the form of a prosthesis or harvested artery or vein to reroute blood flow around the occlusion and restore adequate blood flow to the heart muscle. This treatment is known as coronary artery bypass grafting (CABG).

In the conventional CABG, a large incision is made in the chest and the sternum is sawed in half to allow access to the heart. In addition, a heart lung machine is used to circulate the patient's blood so that the heart can be stopped and the anastomosis can be performed. In order to minimize the trauma to the patient induced by conventional CABG, less invasive techniques have been developed in which the surgery is performed through small incisions in the patient's chest with the aid of visualizing scopes. Less invasive CABG can be performed on a beating or stopped heart and thus may avoid the need for cardiopulmonary bypass.

In both conventional and less invasive CABG procedures, the surgeon has to suture one end of the graft vessel to the coronary artery and the other end of the graft vessel to a blood supplying vein or artery. The suturing process is a time consuming and difficult procedure requiring a high level of surgical skill. In order to perform the suturing of the graft to the coronary artery and the blood supplying artery the surgeon must have relatively unobstructed access to the anastomosis site within the patient. In the less invasive surgical approaches, some of the major coronary arteries cannot be easily reached by the surgeon because of their location. This makes suturing either difficult or impossible for some coronary artery sites. In addition, some target vessels, such as heavily calcified coronary vessels, vessels having very small diameter, and previously bypassed vessels may make the suturing process difficult or impossible.

An additional problem with CABG is the formation of thrombi and atherosclerotic lesions at and around the grafted artery, which can result in the reoccurrence of ischemia. The thrombi and atherosclerotic lesions may be caused by the configuration of the sutured anastomosis site. For example, an abrupt edge at the anastomosis site may cause more calcification than a more gradual transition.

Accordingly, it would be desirable to provide a sutureless vascular anastomosis device which easily connects a graft to a target vessel. It would also be desirable to provide a sutureless anastomosis device which is formed of one piece and is secured to the target vessel in a single step.

SUMMARY OF THE INVENTION

The present invention relates to an anastomosis device for connecting of a graft vessel to a target vessel. The device includes at least two spreading members being substantially in a plane in an undeployed state. The spreading members move out of the plane to support an opening in a target vessel in a deployed state.

In accordance with an additional aspect of the present invention, an anastomosis device for connecting a graft vessel to a target vessel includes a frame for receiving and holding a graft vessel, and first and second spreading members configured to be inserted into a target vessel. At least one of the spreading members is movably connected to the frame and allows movement of the spreading members with respect to each other. The frame is deformable and deformation of the frame moves the spreading members.

According to a further aspect of the invention, an anastomosis device for connecting a graft vessel to a target vessel includes a frame for receiving and holding a graft vessel, and first and second spreading members configured to be inserted into a target vessel. At least one of the spreading members is movably connected to the frame and allows movement of the spreading members with respect to each other. Features are provided on the spreading members for moving the spreading members with respect to the frame.

In accordance with another aspect of the invention, an anastomosis device for connecting a graft vessel to a target vessel includes a frame for receiving and holding a graft vessel, and first and second spreading members configured to be inserted into a target vessel. At least one of the spreading members is movably connected to the frame allows movement of the spreading members with respect to each other. The frame includes features for deforming the frame to move the spreading members.

In accordance with another aspect of the invention, an anastomosis device for connecting a graft vessel to a target vessel includes a plurality of linkages arranged in two rows for grasping opposite sides of an opening in the target vessel. Each of the plurality of linkages include a plurality of angled struts surrounding a bendable central strut. Two end members are connected to opposite ends of the two rows which when moved away from one another expand the linkages and cause the bendable central struts to bend, folding a portion of the linkages outward to trap vessel walls on opposite sides of the opening in the target vessel.

In accordance with another aspect of the present invention, a method of performing anastomosis includes the steps of providing a one-piece anastomosis device, everting an end of a graft vessel around a first portion of the anastomosis device, inserting a second portion of the anastomosis device into an opening in a side wall of a target vessel, and pivoting the first portion with respect to the second portion to capture edges of the opening in the target vessel with the anastomosis device such that a fluid passage is established between the graft and the target vessel.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

The present invention relates to an anastomosis device and method for connecting a graft vessel to a target vessel without the use of conventional sutures. The device according to the present invention greatly increases the speed with which anastomosis can be performed over prior art suturing methods. In addition, the anastomosis device provides a smooth transition between the graft vessel and the target vessel. The devices according to the present invention are particularly designed for use in connecting graft vessels to small target vessels having relatively small diameters such as the coronary arteries. Suture of these small vessels is difficult with conventional techniques, particularly in minimally invasive procedures where space may be limited. The devices may also be used for connecting graft vessels to larger target vessels.

Figure 1:
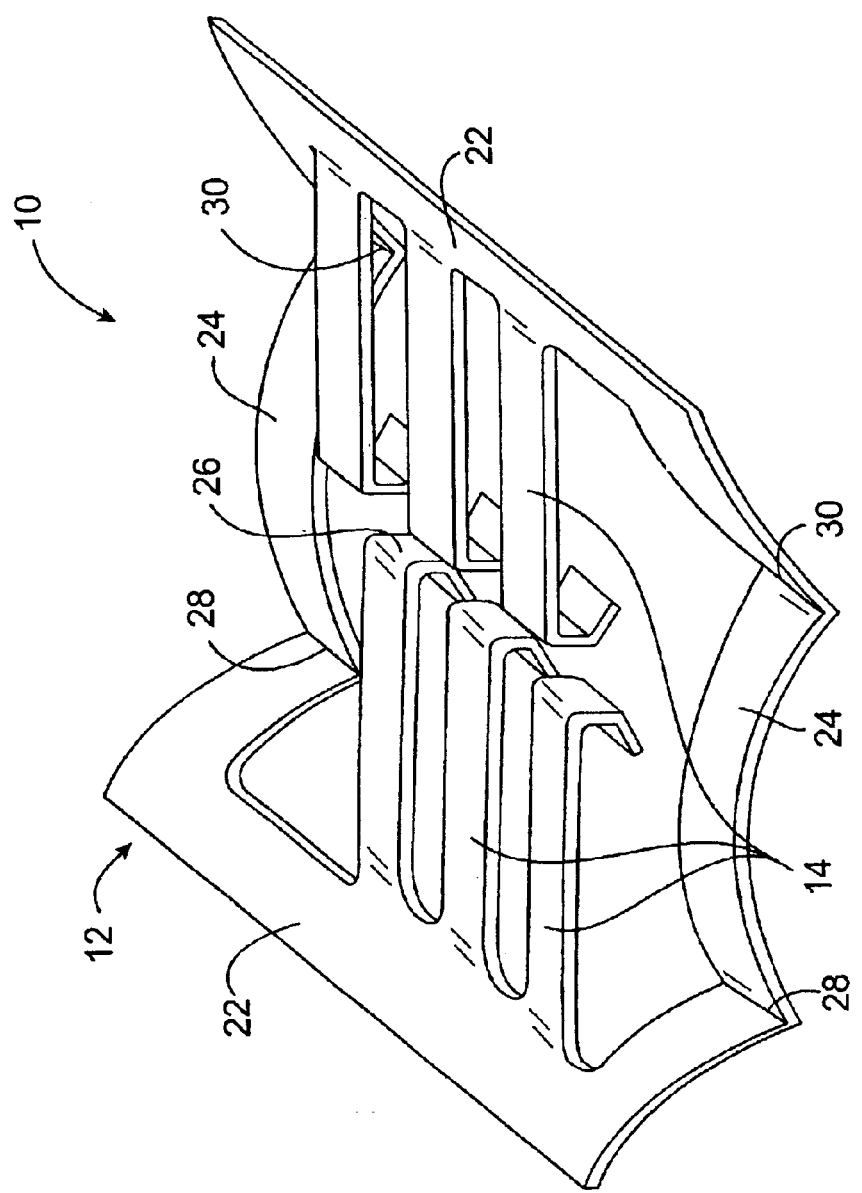
FIG. 1 is a perspective view of a first embodiment of an anastomosis device in a configuration prior to use.

FIG. 1 illustrates an anastomosis device 10 according to a first embodiment of the present invention. The anastomosis device 10 includes a frame 12 and a plurality of fingers 14 extending from the frame. In use, an end of a graft vessel is inserted through the center of the device and everted around the frame 12. The fingers 14 are used as spreading members which are inserted into an opening in the target vessel and pulled away from one another to stretch and capture the edges of the opening in the target vessel.

Figure 2:
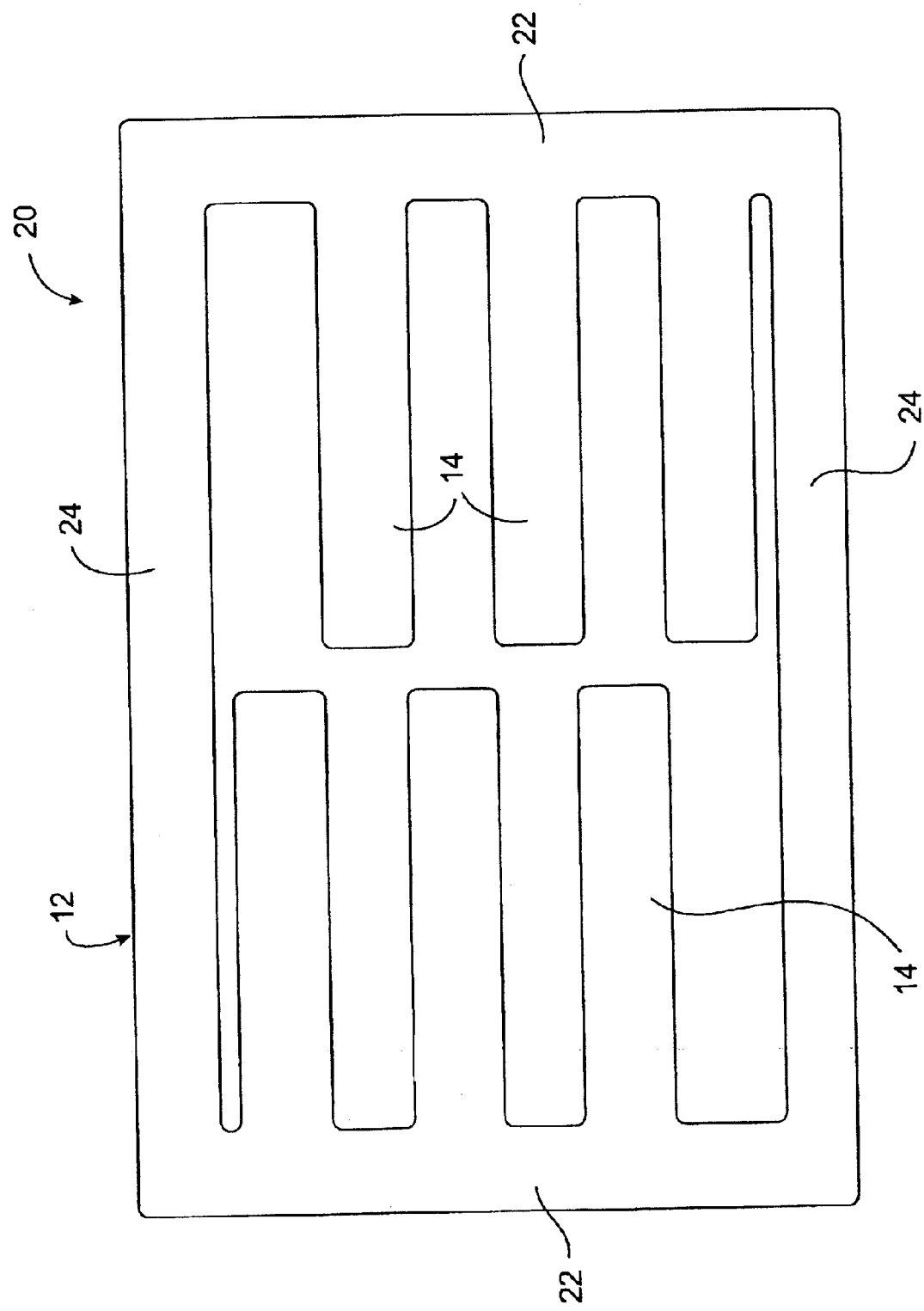
FIG. 2 is a top view of a preformed blank for forming the anastomosis device of FIG. 1.

FIG. 2 illustrates a blank 20 from which the anastomosis device 10 of FIG. 1 is formed. The blank includes the frame 12 having two parallel side beams 22 and two parallel end beams 24. The fingers 14 extend from the side beams 22. Preferably, the fingers 14 extending from one of the side beams 22 are staggered from the fingers extending from the other side beam as illustrated in FIG. 2. The preferred staggered arrangement of the fingers allows the device to be bent so that the fingers 14 extending from one of the side beams 22 extend into a gap between the fingers extending from the opposite side beam. As shown in FIG. 1, the free ends of each of the fingers 14 are bent into a J-shaped hook 26 which is used to grasp and spread the edges of an opening formed in a target vessel. The end beams 24 of the anastomosis device 10 are bent into a W-shape having a first bend 28 and a second bend 30. The first and second bends 28, 30 function as pivots or living hinges which allow the fingers 14 extending from the first side beam 22 to spread away from the fingers extending from the second side beam.

Figure 3:
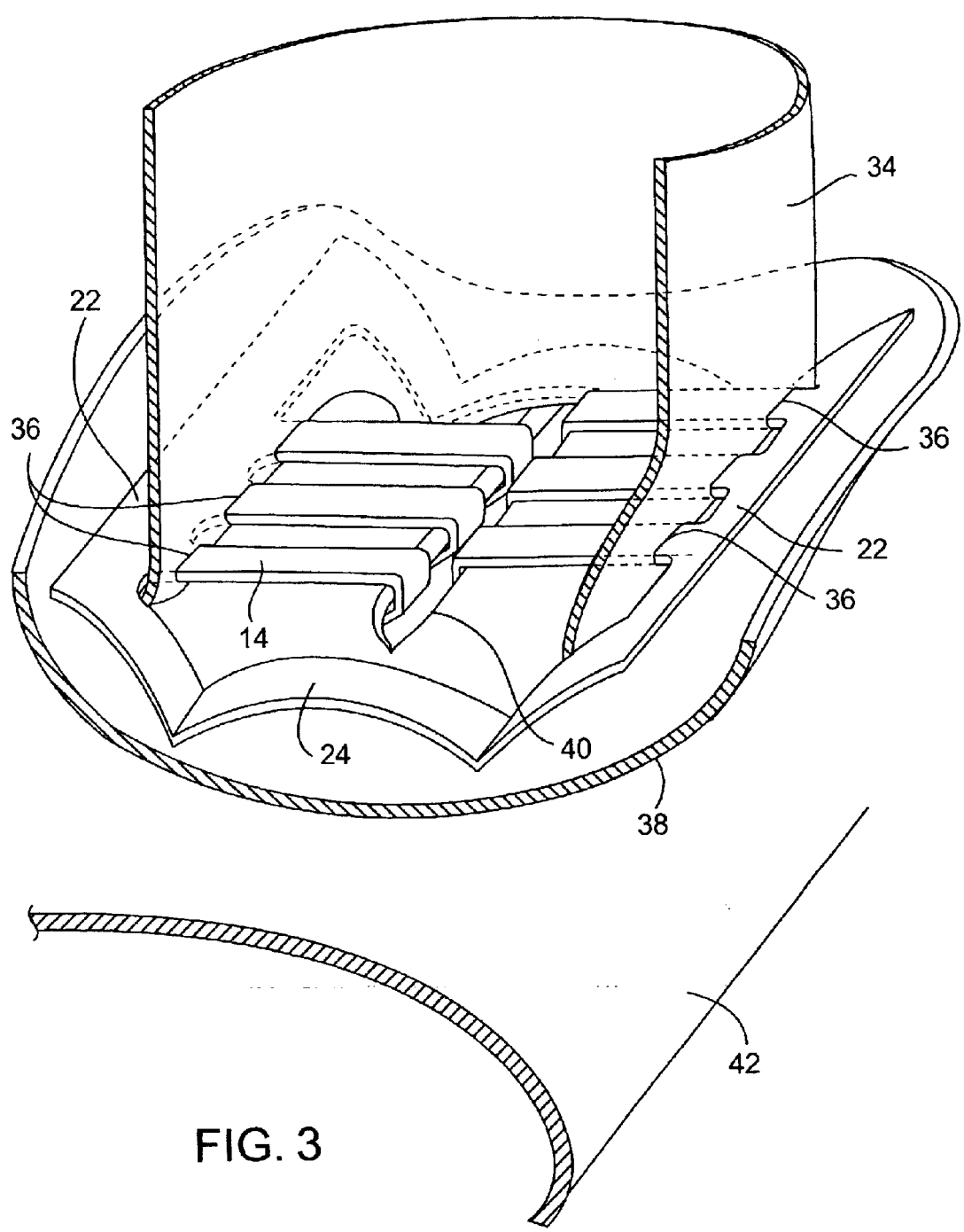
FIG. 3 is a perspective view of the anastomosis device of FIG. 1 with a partially cut away graft vessel wrapped around the device and the device fingers inserted into an opening in the target vessel.

FIG. 3 illustrates the anastomosis device 10 with an end of a graft vessel 34 everted about the frame 12. Six slots 36 are formed in the graft vessel 34 so that the fingers 14 can extend through the graft vessel when the vessel is everted around the frame 12. As shown in FIG. 3, an end 38 of the graft vessel 34 extends underneath and around the side beams 22 and the end beams 24 of the frame 12. The J-shaped hooks 26 of the fingers 14 are arranged substantially in a plane and inserted into an opening 40 or incision in the wall of a target vessel 42. The opening 40 is preferably formed longitudinally along the target vessel 42.

Figure 4:
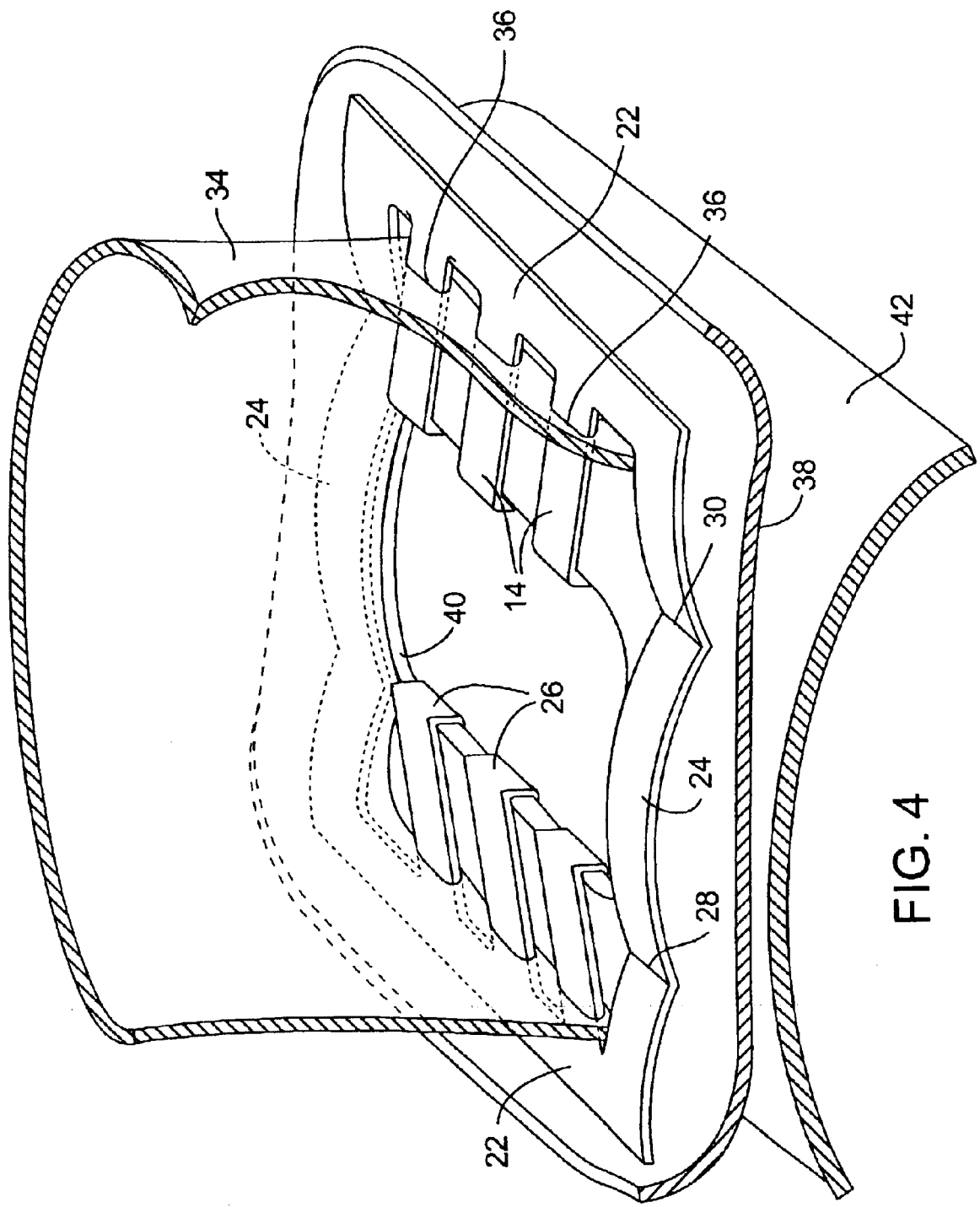
FIG. 4 is a perspective view of the anastomosis device of FIG. 1 with the fingers spread to secure the graft vessel to the target vessel.

FIG. 4 illustrates the completed connection between the graft vessel 34 and the target vessel 42 with the anastomosis device 10. In particular, the device 10 of FIG. 3 has been bent so that the side beams 22 are pivoted outward and the angles of the first bend 28 and the second bend 30 are substantially straightened. As the bends 28, 30 in the frame 12 are straightened, the J-shaped hooks 26 of the fingers 14 move away from one another and out of the original insertion plane to stretch and capture the edges of the opening 40 in the target vessel 42. As illustrated in FIG. 4, the anastomosis device 10 presses the edges of the graft vessel 34 against an exterior surface of the target vessel 42 around the opening 40 in the side of the target vessel.

Although the embodiment of FIGS. 1–4 has been illustrated with three fingers 14 extending from each of the side beams 22, it should be understood that other numbers of fingers may also be used without departing from the present invention. As illustrated in FIG. 4, only a small amount of metal of the anastomosis device comes in contact with the blood. In particular, the fingers 14 extending through the slots 36 in the side walls of the graft vessel 32 come into contact with the blood while the remainder of the anastomosis device is outside of the blood flow area.

Preferably, the finger linkage anastomosis device of FIGS. 1–4 is cut from a metal tube such as a steel tube and is then formed into the shape illustrated in FIG. 1 by bending. The fingers 14 are interlaced and the free ends of the fingers are bent downwards into the J-shaped hooks 26. The graft vessel 34 is initially pulled between the fingers and pierced by the fingers to form the slots 36. The end of the graft vessel 34 is wrapped around the frame 12. To attach the graft vessel 34 to the target vessel 42, the J-shaped hooks 26 are inserted into the incision 40 in the target vessel. When the side beams 22 are rotated outwards, the J-shaped hooks 26 open the incision 40 in the target vessel 42 and secure the graft vessel 34 to the target vessel. Rotation of the side beams 22 of the frame 12 causes plastic deformation of the anastomosis device primarily at the first and second bends 28, 30 and seals the graft vessel 34 against the exterior of target vessel 42.

Figure 5:
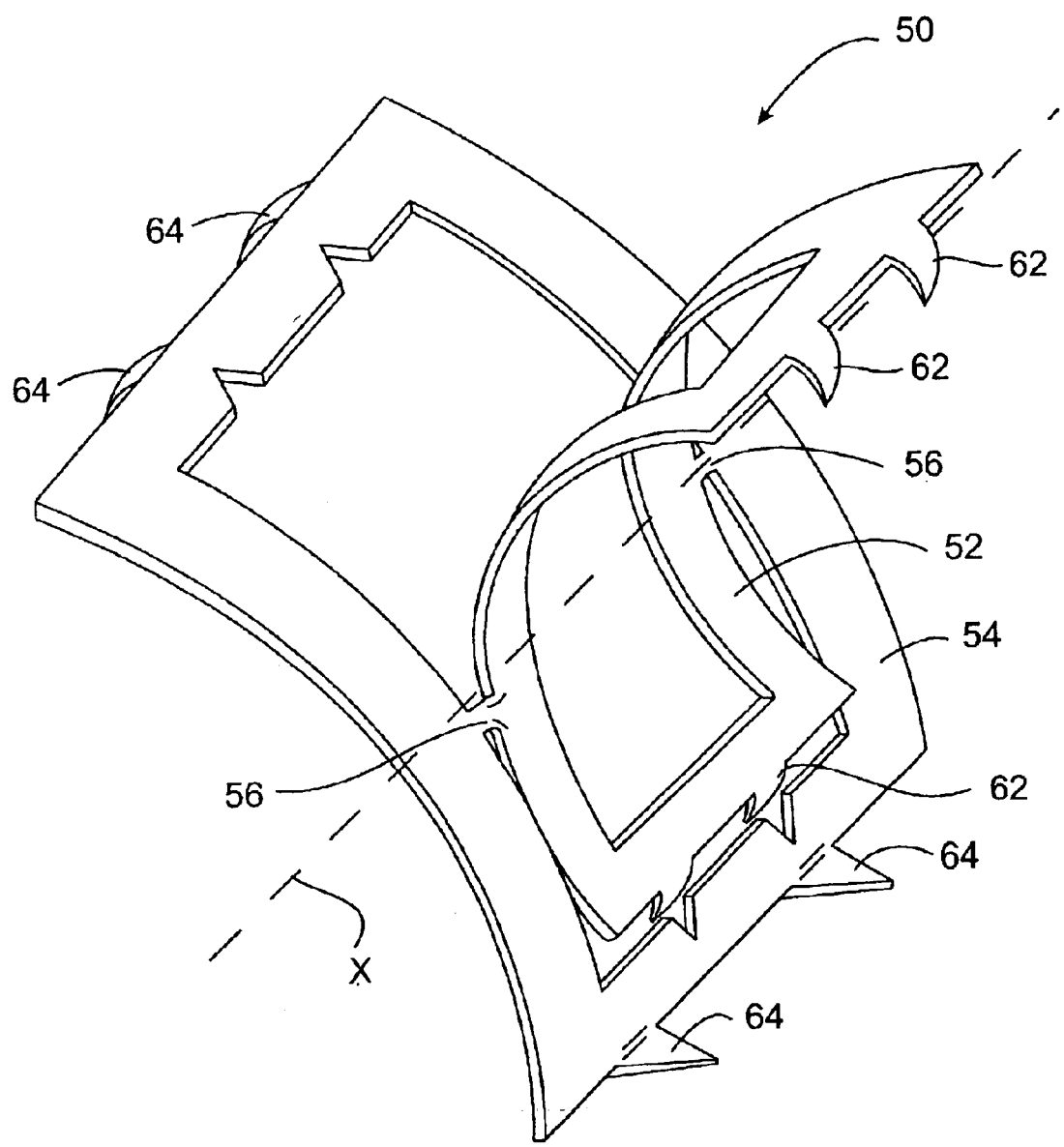
FIG. 5 is a perspective view of an alternative embodiment of an anastomosis device prior to use.

FIG. 5 illustrates an alternative embodiment of an anastomosis device 50 having a single scissor configuration. The anastomosis device 50 according to FIG. 5 includes an inner loop 52 connected to an outer loop 54 by two hinges 56.

Figure 6:
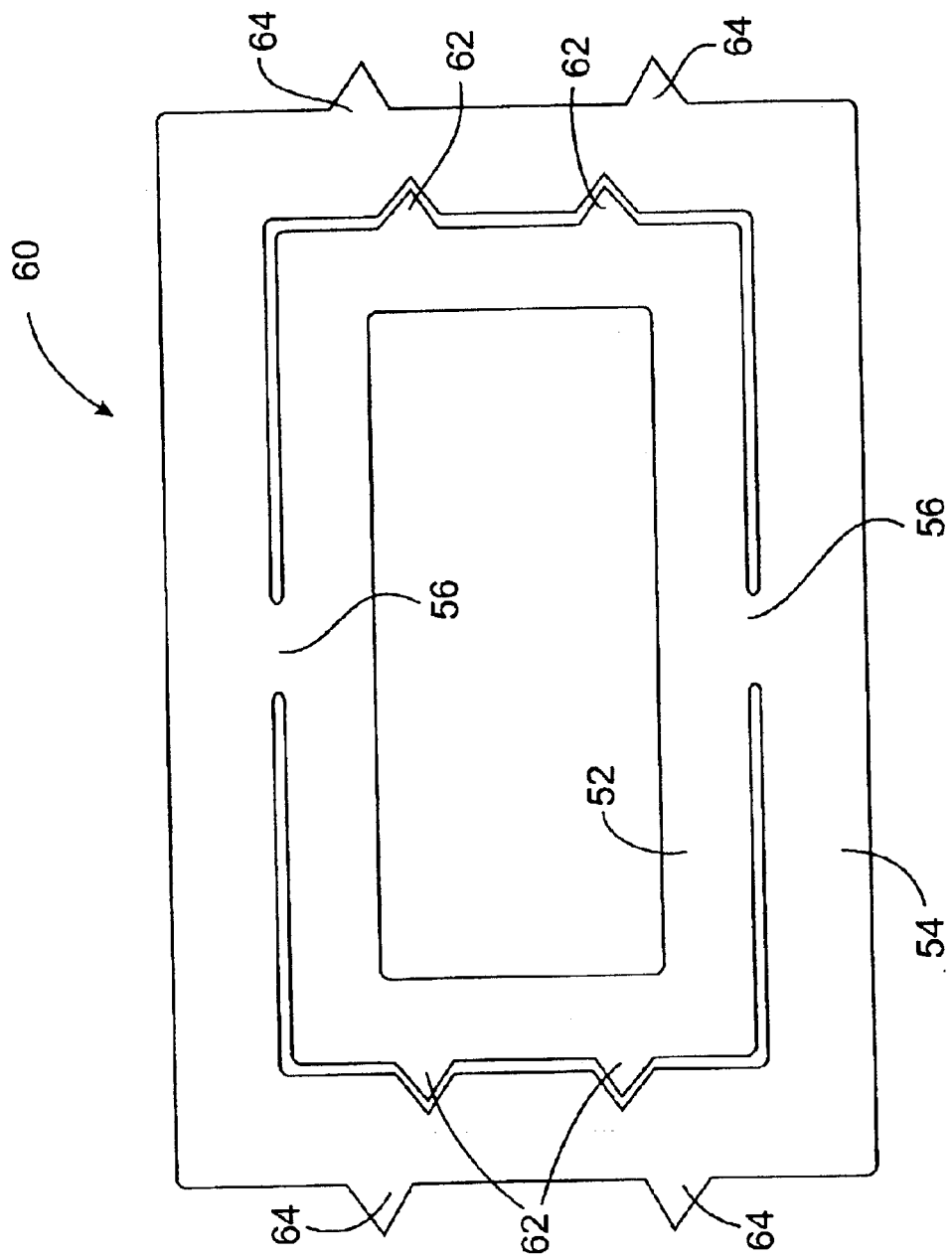
FIG. 6 is a top view of a preformed blank from which the anastomosis device of FIG. 5 is formed.

FIG. 6 illustrates a flat plan view of a blank 60 for forming the anastomosis device 50. The blank 60 includes the inner loop 52 and the outer loop 54 connected by the two hinges 56. The inner loop 52 has two teeth 62 extending from opposite ends of the inner loop. In addition, the outer loop 54 has two teeth 64 extending from each end of the outer loop. As illustrated in FIG. 5, the teeth 62, 64 are bent to grasp and hold the graft and target vessels together. The anastomosis device 50 of FIG. 5 is preferably cut from a tube and bent into the shape illustrated in FIG. 5. The inner loop 52 is connected to the outer loop 54 at the hinges 56 which are positioned along a bending axis X of the device. Prior to use, the blank 60 including the inner and outer loops 52, 54 is bent in a C-shape and the inner and outer loops are pivoted so that the C-shapes face opposite directions.

Figure 7:
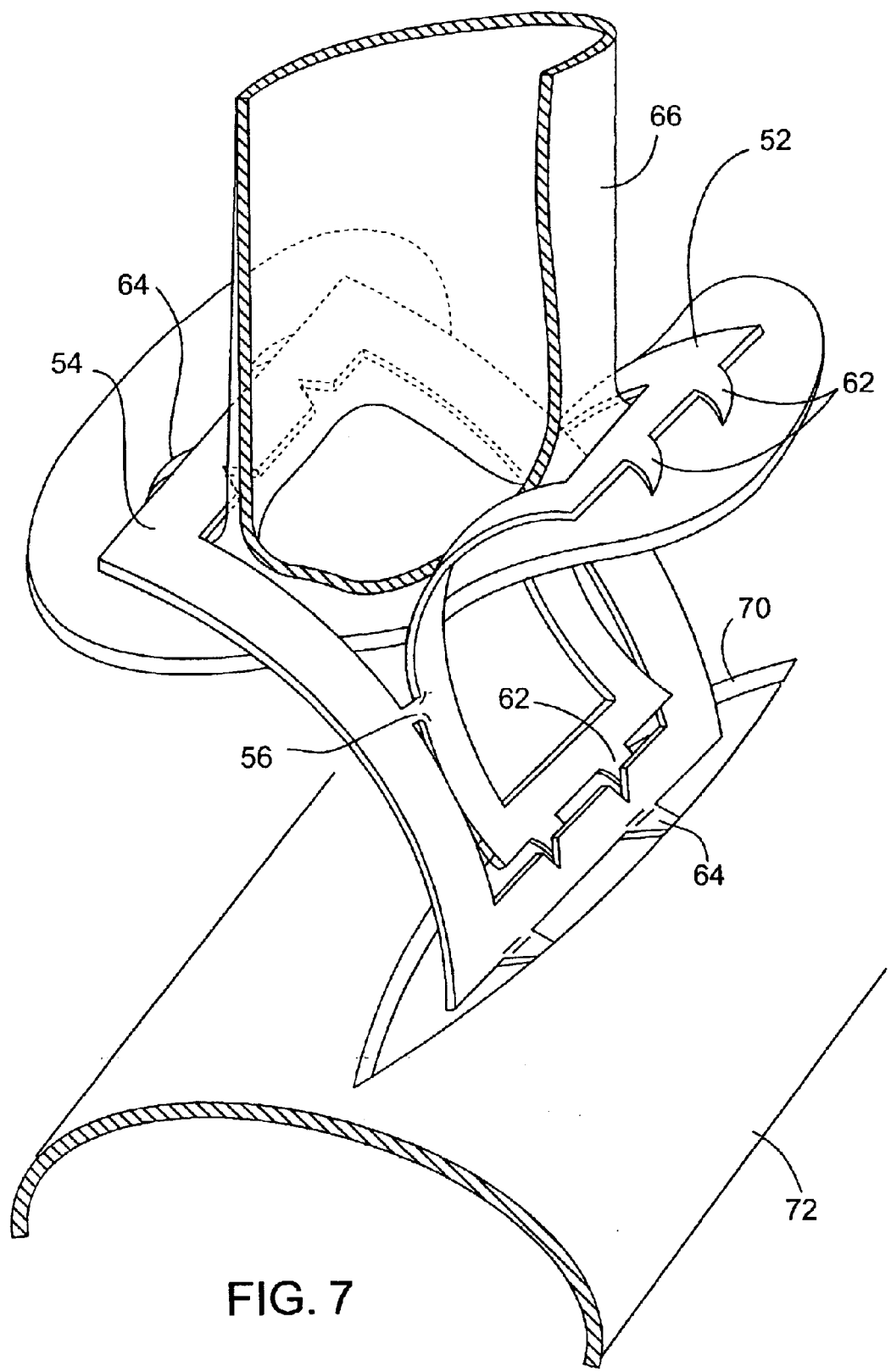
FIG. 7 is a perspective view of the anastomosis device of FIG. 5 with the a partially cut away graft vessel wrapped around the device and the device being inserted into an opening in the target vessel.
Figure 8:
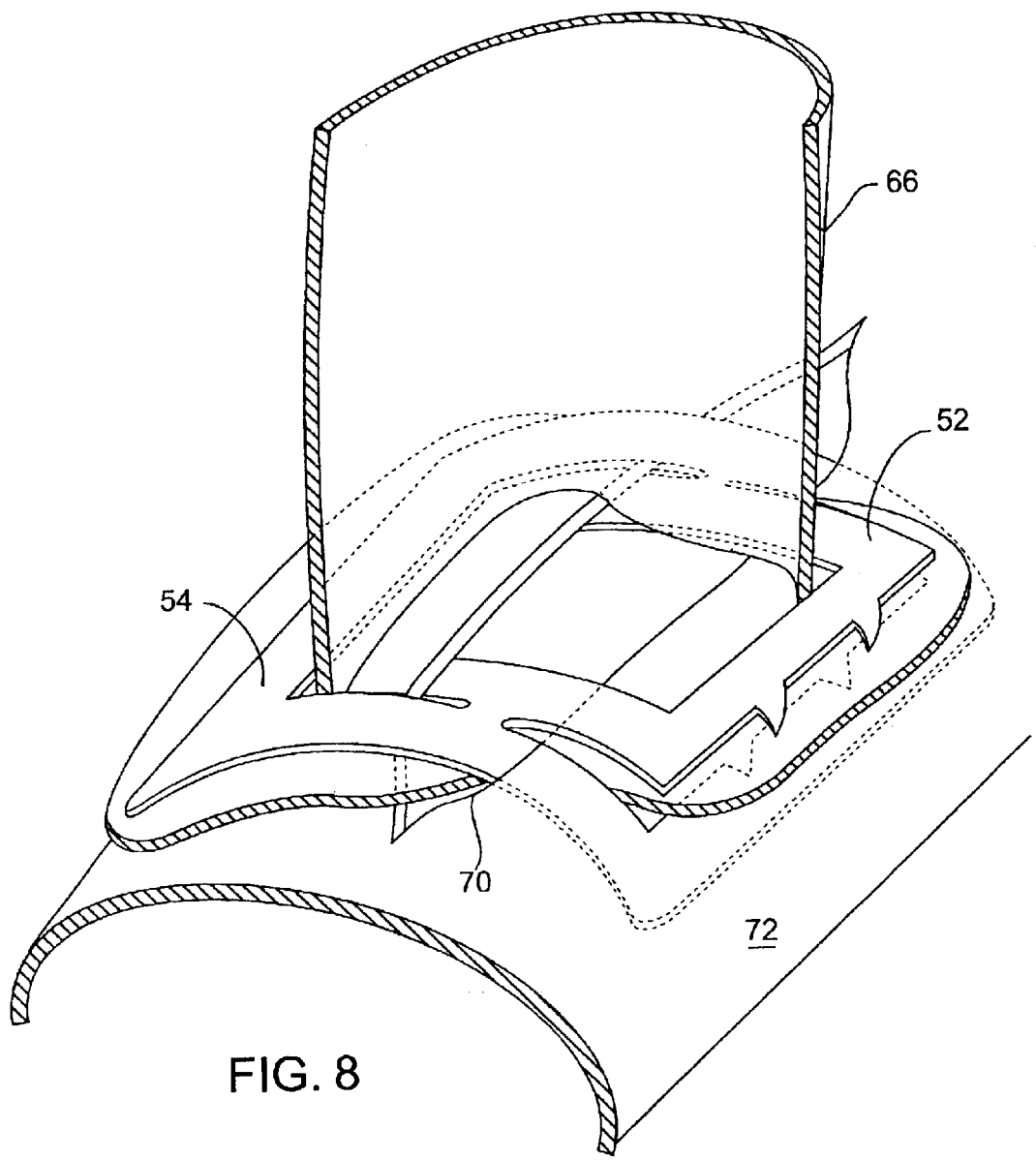
FIG. 8 is a perspective view of the anastomosis device of FIG. 5 securing a graft vessel to a target vessel.

As illustrated in FIG. 7, the graft vessel 66 is inserted between the inner and outer loops 52, 54 and everted over the upper ends of the inner and outer loops such that ends of the graft vessel 66 become caught on the teeth 62, 64. The lower end of the device is arranged substantially in a plane and is inserted through an opening 70 in the target vessel 72 with the teeth 62, 64 on the lower end of the device pointing outward. The upper ends of the inner and outer loops 52, 54 are then pivoted away from one another to seat the device into the inner wall of the target vessel and secure the graft vessel 66 to the target vessel 72 as illustrated in FIG. 8. The pivoting action of the anastomosis device of FIG. 5 is similar to the pivoting action of scissors being opened and moves the lower ends of the inner and outer loops 52, 54 out of the insertion plane. As illustrated in FIG. 8, once the graft vessel 66 and target vessel 72 have been connected with the anastomosis device 50, the edges of the everted graft vessel and the side walls of the target vessel 72 around the opening 70 are both grasped between the inner and outer loops 52, 54 of the frame on either side of the opening 70.

Figure 9:
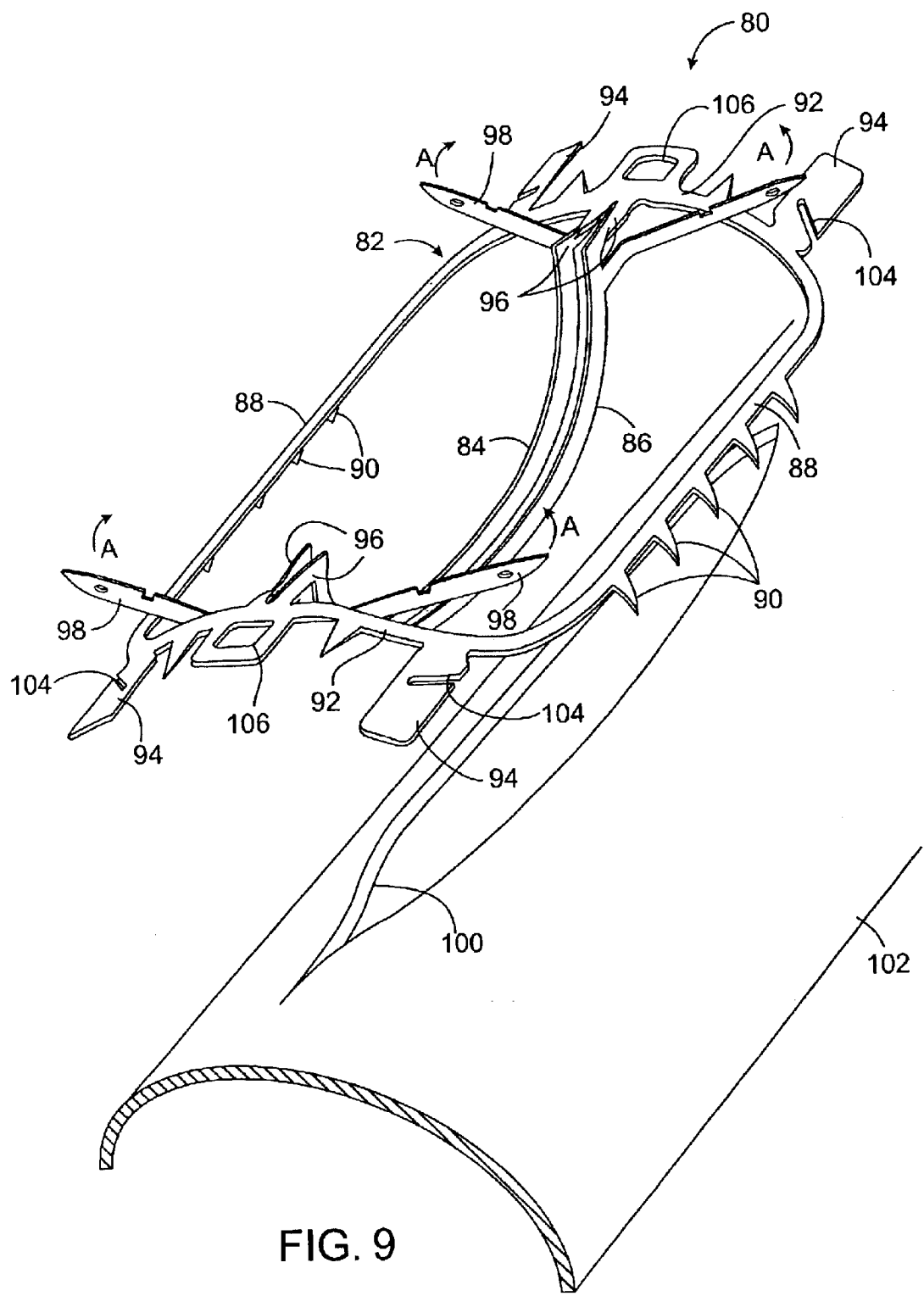
FIG. 9 is a perspective view of another alternative embodiment of an anastomosis device prior to use.

FIG. 9 illustrates an alternative embodiment of an anastomosis device 80 having two pivoting members or a double scissor arrangement. The anastomosis device 80 includes a frame 82 and first and second pivoting U-shaped members 84, 86. The frame 82 includes side beams 88 having barbs 90 extending downward from an exterior edge of the side beams. The side beams are connected by end beams 92. Extending from the side beams 92 are four locking tabs 94. The first and second pivoting U-shaped members 84, 86 are connected on either end to a central portion of the end beams 92 by pivot joints 96. Two lever arms 98 extend from each of the U-shaped members 84, 86 adjacent the pivot joints 96.

In use, an end of a graft vessel (not shown) is inserted into the center of the frame above the U-shaped members 84, 86 and wrapped around or everted over the barbs 90 on the side beams 88. The U-shaped members 84, 86 are arranged in a substantially parallel configuration as shown in FIG. 9 and are substantially in a plane for insertion into a slit shaped opening 100. The U-shaped members 84, 86 are inserted through the opening 100 or incision in the target vessel 102. The two lever arms 98 are then each rotated in the direction of the corresponding arrows A in FIG. 9 to pivot the U-shaped members 84, 86 at the pivot joints 96 moving the U-shaped members out of the insertion plane. The opened U-shaped members 84, 86 clamp the side wall of the target vessel 102 between the U-shaped members and the side beams 88 of the frame 82. The lever arms 98 are then folded down and locked in place by folding up the four locking tabs 94 and sliding the lever arms into slots 104 in the tabs.

Figure 10:
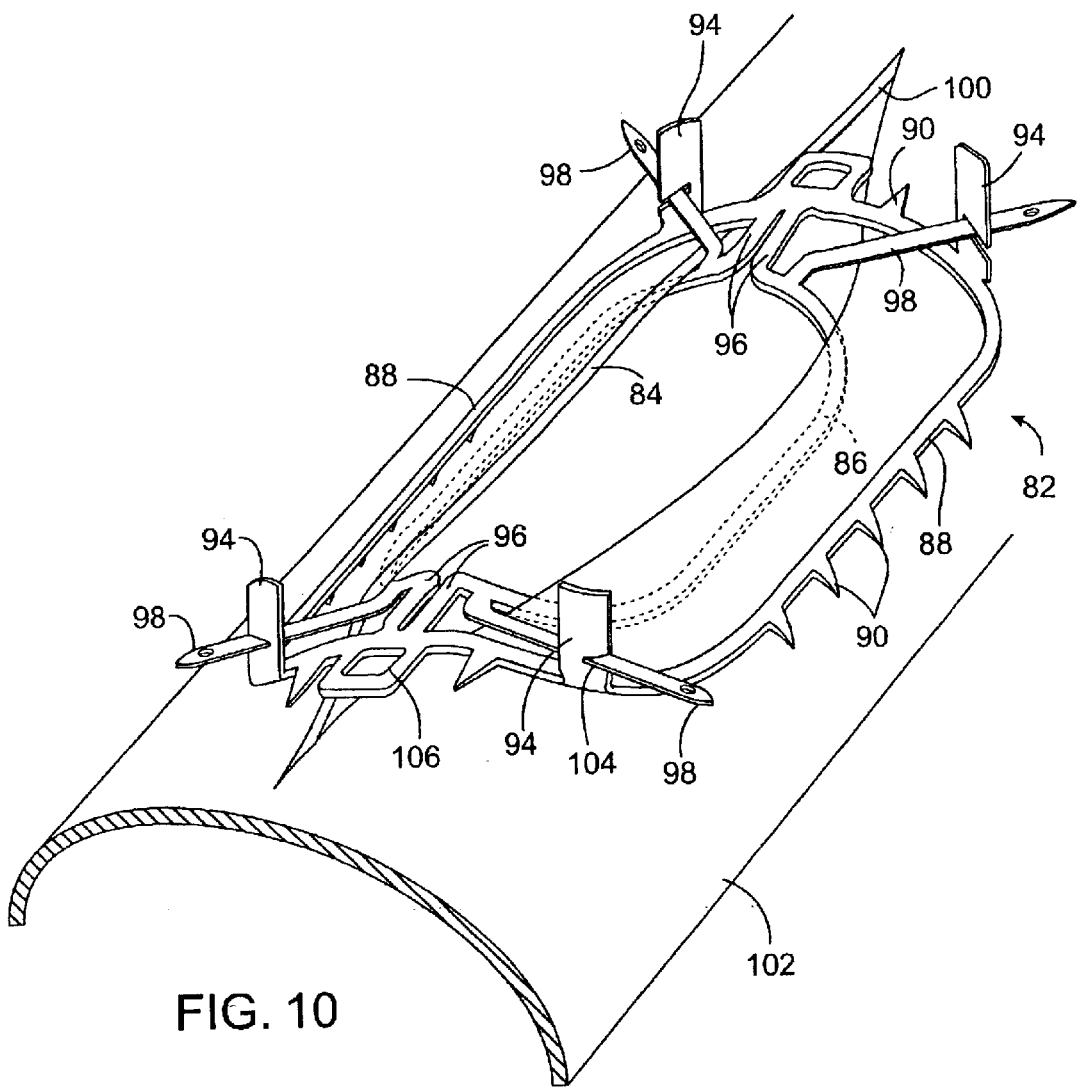
FIG. 10 is a perspective view of the anastomosis device of FIG. 9 secured to the target vessel with the graft vessel omitted for clarity.

The graft vessel has been omitted from FIGS. 9 and 10 for purposes of clarity. However, it should be understood that the end of the graft vessel as well as the edges of the opening 100 in the target vessel 102 are captured between the frame 82 and the U-shaped pivoting members 84, 86. The square holes 106 in the ends of the frame 82 may be used by an inserting device to grasp the anastomosis device 80. The edges of the pivoting U-shaped members 84, 86 may include serrated edges for incising a target vessel to form the opening 100 in the target vessel.

Figure 11:
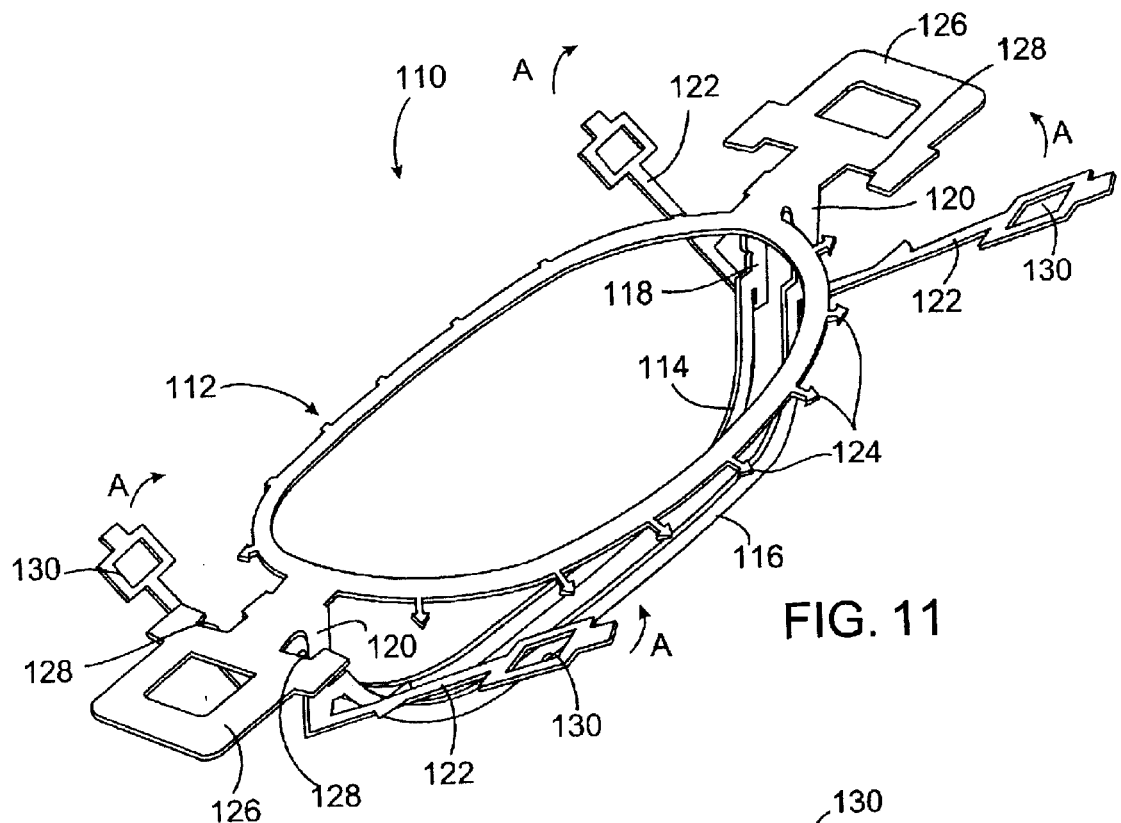
FIG. 11 is a perspective view of a further alternative embodiment of an anastomosis device prior to use.
Figure 12:
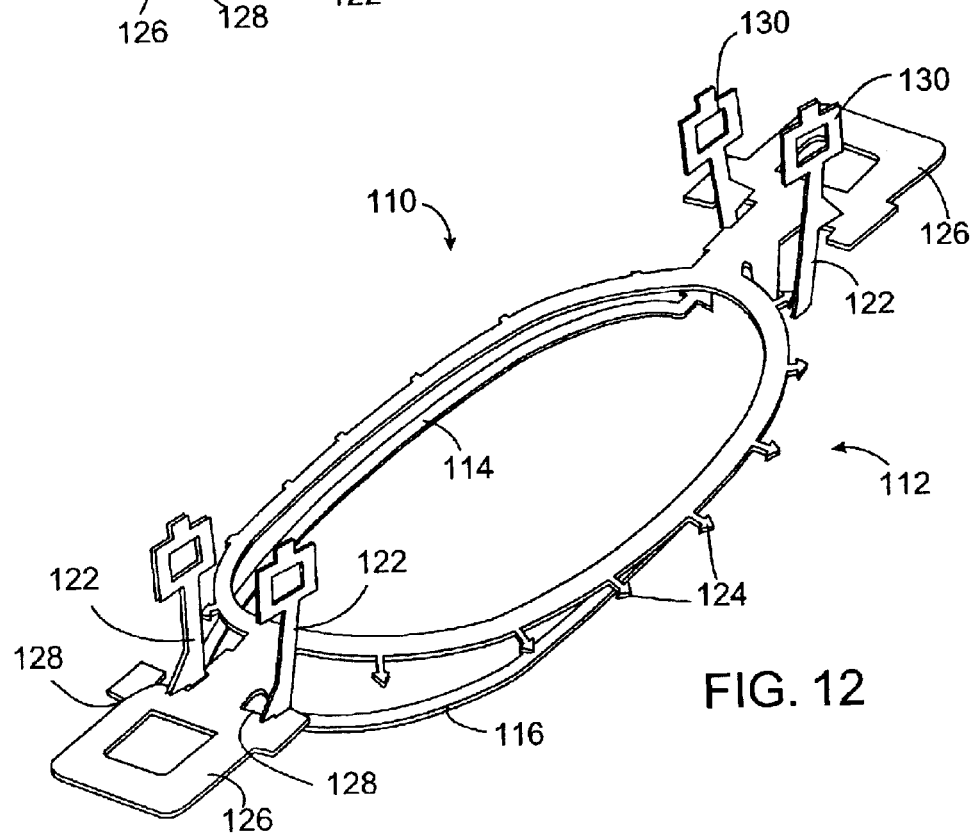
FIG. 12 is a perspective view of an anastomosis device of FIG. 11 in a closed position in which the device is used to connect a graft vessel to a target vessel.

FIGS. 11–12 show a variation of the double scissor arrangement for an anastomosis device of FIG. 9. The anastomosis device 110 of FIG. 11 includes a frame 112, and first and second pivoting U-shaped members 114, 116. The U-shaped members 114, 116 are joined to the frame 112 by pivots or living hinges 118. The pivots 118 are offset vertically from the frame 112 by offset arms 120. The offset arms 120 preferably have a length which is substantially equal to a thickness of the target vessel wall. Two lever arms 122 extend from each of the first and second U-shaped members 114, 116. The lever arms 122 are rotated in the direction of the arrows A to pivot the U-shaped members 114, 116 about the pivots 118 and trap the side walls of the target vessel between the U-shaped members 114 116 and the frame 112. The lever arms 122 may be provided with rectangular openings 130 which are used by an associated deployment device to manipulate the lever arms 122.

According to the embodiment of FIGS. 11–12, the frame 112 is provided with a plurality of points 124 on an exterior surface of the frame 112 which hold the everted graft vessel to the frame 112. Once the graft vessel is punctured by the points 124, the graft vessel cannot slip off the points 124. The frame 112 includes locking tabs 126 at either end having recesses 128 for receiving the lever arms 122 in a locked position as illustrated in FIG. 12.

Figure 13:
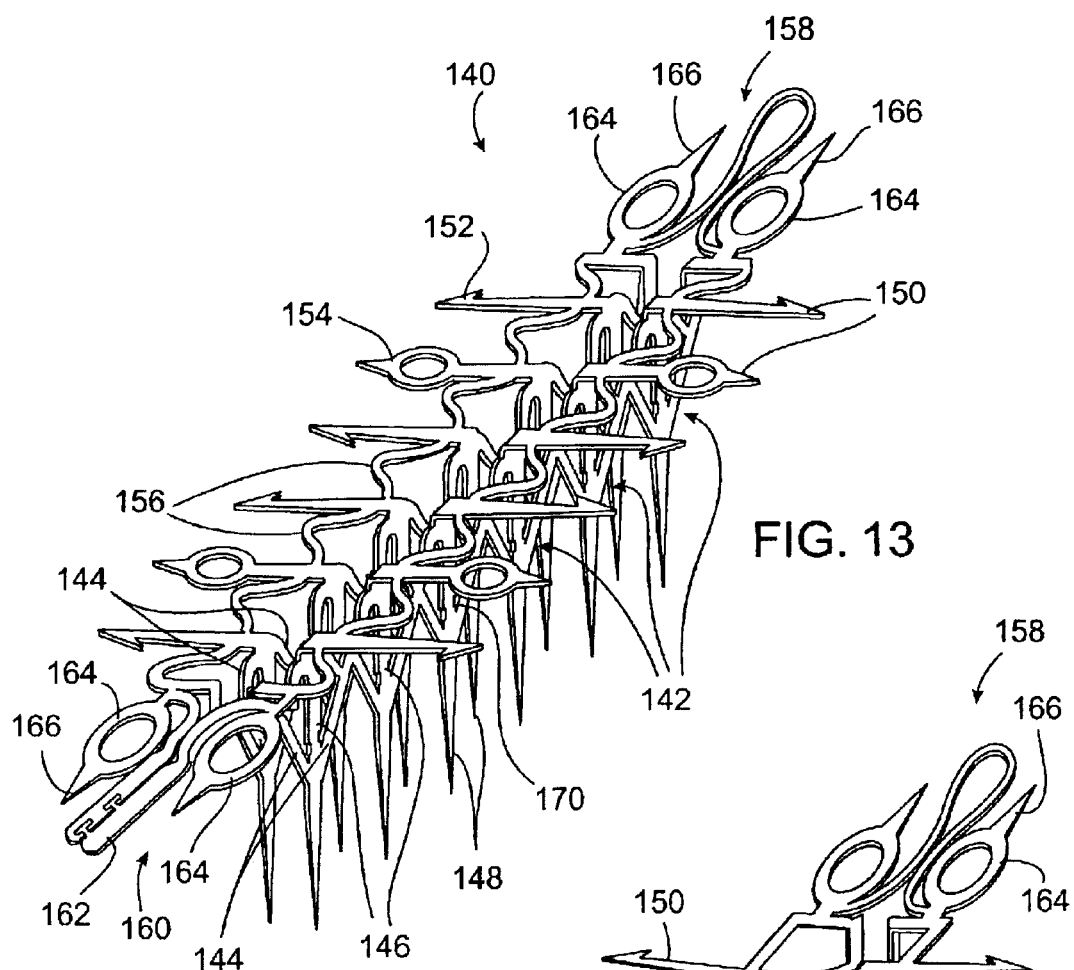
FIG. 13 is a perspective view of an additional embodiment of an anastomosis device with an expandable linkage for deployment shown prior to use.
Figure 14:
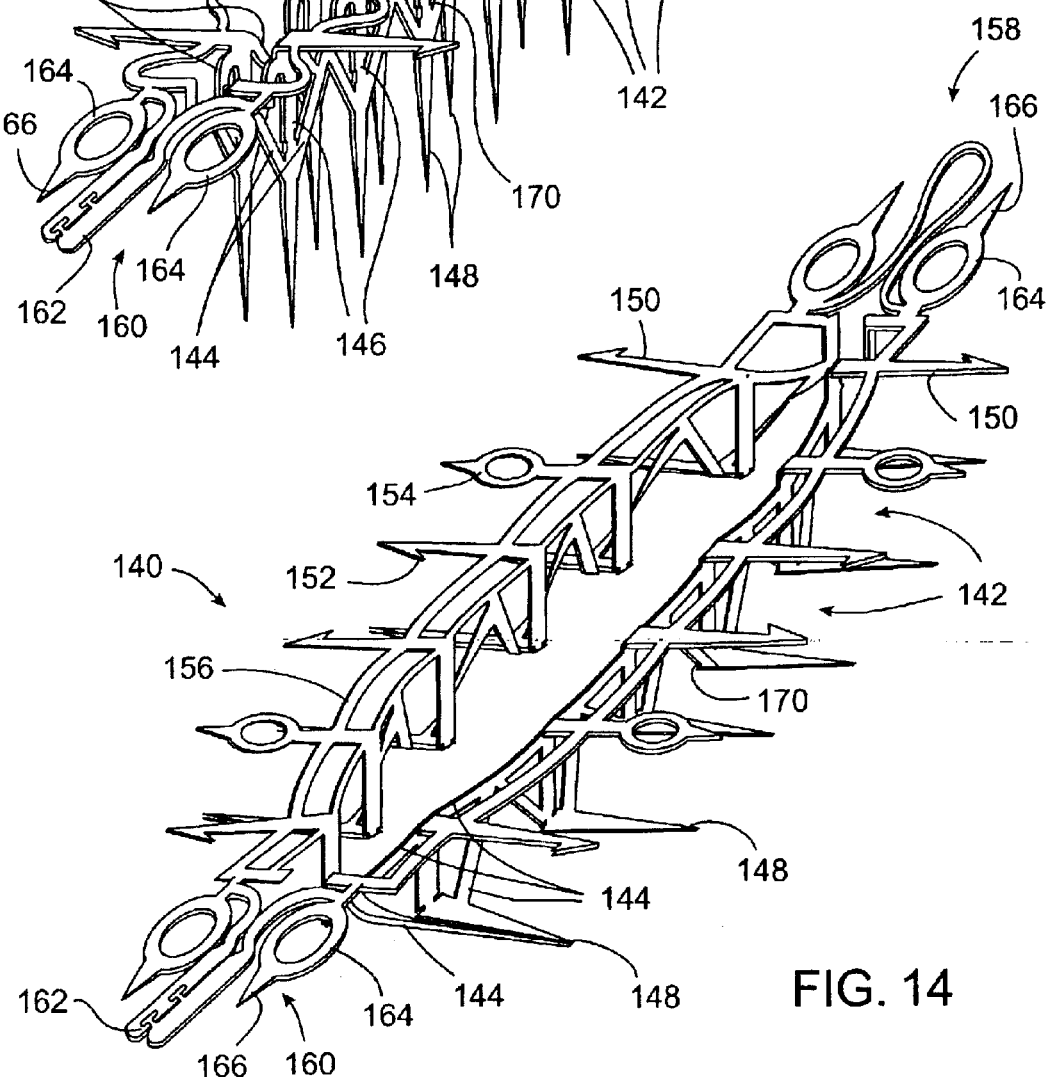
FIG. 14 is a perspective view of the anastomosis device of FIG. 13 in an expanded position in which the device is used to connect a graft vessel to a target vessel.

FIGS. 13–14 illustrate an alternative embodiment of an anastomosis device 140 which is longitudinally expandable to cause a lower portion of the device 140 to fold outward, trapping the walls of the target vessel with the device 140. The anastomosis device 140 includes a plurality of linkages 142 which are arranged in two substantially parallel rows. Each of the linkages 142 includes four angled struts 144 which form a substantially diamond shape in the configuration of FIG. 13 and vertical bendable struts 146 positioned vertically in the center of each of the diamonds formed by the angled struts 144. Each of the linkages 142 also includes a lower prong 148 arranged substantially vertically for insertion into an opening in the target vessel and an upper prong 150 which is oriented substantially perpendicular to the lower prong 148 in the insertion configuration of FIG. 13. The upper and/or lower prongs 148, 150 may include barbs 152. Some of the upper prongs 150 may include loops 154 or other grasping members which can be used by a deployment tool to grasp the anastomosis device 140 during insertion and deployment. Finally, each of the linkages 142 includes one or more stabilizing struts 156. The stabilizing struts 156 may have a curved configuration to allow longitudinal expansion of the anastomosis device 140.

The anastomosis device 140 includes end members 158, 160 which connect the ends of the two rows of linkages 142. The end members 158, 160 may take on many different configurations. In the example of the anastomosis device 140 illustrated in FIGS. 13–14, the device is formed from a continuous sheet of material. Therefore, the end member 158 is folded to align the first and second rows with one another while the second end member 160 includes a lock member 162 which holds the ends of the rows of linkages together. Each of the end members includes one or more loops 164 or grasping members which are grasped by a deployment tool. The end members 158, 160 also preferably include prongs 166 to help grasp the tissue of the evened graft vessel.

In use, a graft vessel (not shown) is inserted through a center of the anastomosis device 140 and an end of the graft vessel is evened over the lower prongs 148 of the device. The graft vessel may also be evened over the upper prongs 150 and the end member prongs 166. The prongs 148, 150, 166 pierce through the graft vessel to securely hold the graft vessel in place in the anastomosis device 140. Once the graft vessel has been loaded onto the anastomosis device 140, the lower prongs 148 of the device 140 which are positioned substantially in a plane and the evened end of the graft vessel are inserted through a slit shaped opening in the target vessel. The loops 164 on the end members 158, 160 are then used to expand the device in a longitudinal direction with a deployment tool or manually. The longitudinal expansion of the device of FIG. 13 causes each of the diamond shaped linkages 142 of angled struts 144 to expand longitudinally and causes the bendable vertical struts 146 to bend at their hinges 170.

The expanded configuration of the anastomosis device 140 is illustrated in FIG. 14. The anastomosis device deployment tool may also expand the device 140 in a direction transverse to the longitudinal direction of the device 140 to enlarge the opening of the target vessel for increased blood flow. Once deployment of the anastomosis device 140 is complete, the wall of the target vessel around the opening in the target vessel is trapped between the upper and lower prongs 148, 150. In the expanded configuration shown in FIG. 14, the upper and lower prongs 148, 150 are preferably substantially parallel. Alternatively, an angle may be formed between the upper and lower rows of prongs 148, 150.

The anastomosis device 140 of FIGS. 13–14 may also be formed as a two-piece device or may be split in half at the ends after deployment. The compliance of a split or two-piece anastomosis device 140 will allow the device and graft site to flex in response to blood flow.

Each of the anastomosis devices described above are preferably single piece devices which are formed by laser cutting or punching from a tube or sheet of material. The devices may be provided in varying sizes to join vessels of different sizes. The teeth, barbs, or points which have been discussed above with regard to the various embodiments may be used in varying numbers and arrangements to help secure the vessels in place.

Although the invention has been principally discussed with respect to coronary bypass surgery, the anastomosis devices of the present invention may be used in other types of anastomosis procedures. For example, the anastomosis device may be used in femoral-femoral bypass, vascular shunts, subclavian-carotid bypass, organ transplants, and the like. The anastomosis device may be used with natural or synthetic graft vessels.

The anastomosis devices may be made of any known material which can be bent and will retain the bent shape such as stainless steel, nickel titanium alloys, and the like. The hinges or pivot joints which have been discussed above in the various embodiments of the present invention may be designed to concentrate the bending at a desired location. For example, the pivot joints 96 of the anastomosis device 80 of FIGS. 9 and 10 may be formed with a thickness or width which is smaller than other portions of the frame and the U-shaped members in order to concentrate the bending in the pivot joints.

While the invention has been described in detail with reference to the preferred embodiments thereof, it will be apparent to one skilled in the art that various changes and modifications can be made and equivalents employed, without departing from the present invention.

What is claimed is:

1. A method for connecting a graft vessel to a target vessel each having a wall surrounding a lumen, the method comprising:

providing a unitary anastomosis device having an outer loop and an inner loop connected to and substantially concentric with said outer loop;

moving at least a portion of said inner loop and at least a portion of said outer loop away from one another;

placing an end of the graft vessel between at least a portion of said inner loop and at least a portion of said outer loop;

making an opening in the side of the target vessel;

positioning the anastomosis device into the opening such that at least a portion of the wall of the target vessel is positioned between at least a portion of said inner loop and at least a portion of said outer loop; and releasing said anastomosis device.

2. The method of claim 1, wherein at least one of said inner loop and said outer loop includes at least one tooth, further comprising grasping tissue with at least one said tooth.

3. The method of claim 1, wherein said placing comprises everting an end of the graft vessel over part of at least one of said inner loop and said outer loop.

4. The method of claim 1, wherein said moving comprises pivoting said inner loop relative to said outer loop.

5. The method of claim 1, wherein said anastomosis device is composed of superelastic material.

6. The method of claim 1, wherein said anastomosis device is composed of stainless steel.

7. The method of claim 1, further comprising deforming said anastomosis device after said positioning.

* * * * *